United States Patent
Yamada et al.

(10) Patent No.: US 10,881,683 B2
(45) Date of Patent: Jan. 5, 2021

(54) NUCLEIC ACID MOLECULE

(71) Applicant: TOHOKU UNIVERSITY, Miyagi (JP)

(72) Inventors: Tetsuya Yamada, Miyagi (JP); Hideki Katagiri, Miyagi (JP); Sohei Tsukita, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 22 days.

(21) Appl. No.: 15/760,861

(22) PCT Filed: Sep. 16, 2016

(86) PCT No.: PCT/JP2016/077575
§ 371 (c)(1),
(2) Date: Mar. 16, 2018

(87) PCT Pub. No.: WO2017/047800
PCT Pub. Date: Mar. 23, 2017

(65) Prior Publication Data
US 2019/0105342 A1   Apr. 11, 2019

(30) Foreign Application Priority Data

Sep. 16, 2015 (JP) ................. 2015-183339

(51) Int. Cl.
A61K 31/711 (2006.01)
G01N 33/15 (2006.01)
A61K 48/00 (2006.01)
A61K 31/7105 (2006.01)
A61P 3/10 (2006.01)

(52) U.S. Cl.
CPC ........ *A61K 31/7105* (2013.01); *A61K 31/711* (2013.01); *A61K 48/00* (2013.01); *A61K 48/0066* (2013.01); *A61P 3/10* (2018.01); *G01N 33/15* (2013.01)

(58) Field of Classification Search
CPC combination set(s) only.
See application file for complete search history.

(56) References Cited

U.S. PATENT DOCUMENTS

| 2006/0185027 | A1* | 8/2006 | Bartel | .............. | C12N 15/111 800/14 |
|---|---|---|---|---|---|
| 2007/0231810 | A1 | 10/2007 | Todd et al. | | |
| 2011/0117565 | A1 | 5/2011 | Zhang et al. | | |
| 2013/0109744 | A1 | 5/2013 | Kunisada et al. | | |
| 2013/0123480 | A1 | 5/2013 | Todd et al. | | |
| 2013/0143314 | A1 | 6/2013 | Shiels et al. | | |
| 2014/0234263 | A1 | 8/2014 | Shiels | | |
| 2015/0258056 | A1 | 9/2015 | Woods et al. | | |
| 2016/0243171 | A1 | 8/2016 | Shiels et al. | | |
| 2016/0312310 | A1 | 10/2016 | Zhang et al. | | |
| 2018/0338997 | A1 | 11/2018 | Shiels et al. | | |
| 2019/0167732 | A1 | 6/2019 | Shiels et al. | | |

FOREIGN PATENT DOCUMENTS

| CN | 101475984 A | 7/2009 |
|---|---|---|
| CN | 103210089 A | 7/2013 |
| CN | 103789311 A | 5/2014 |
| WO | WO-2007/081680 A2 | 7/2007 |
| WO | WO-2008/036765 A2 | 3/2008 |
| WO | WO-2009/143181 A2 | 11/2009 |
| WO | WO-2012/005339 A1 | 1/2012 |
| WO | WO-2012/020307 A2 | 2/2012 |
| WO | WO-2016/081941 A1 | 5/2016 |

OTHER PUBLICATIONS

Nakayama et al. Diabetologia 2009, 52:115-124 (Year: 2009).*
Klein et al. PLoS One 2013 8(1): e55064. doi:10.1371/journal.pone. 0055064 (Year: 2013).*
Extended European Search Report for European Application No. 16846671.2, dated Apr. 24, 2019 (10 pages).
Rome, "Are extracellular microRNAs involved in type 2 diabetes and related pathologies?" Clin Biochem. 46(10-11):937-45 (2013).
Hasegawa et al., "Bone marrow (BM) transplantation promotes beta-cell regeneration after acute injury through BM cell mobilization," Endocrinology. 148(5):2006-2015 (2007).
Hess et al., "Bone marrow-derived stem cells initiate pancreatic regeneration," Nat Biotechnol. 21(7):763-770 (2003).
Nakayama et al., "Impact of whole body irradiation and vascular endothelial growth factor-A on increased beta cell mass after bone marrow transplantation in a mouse model of diabetes inducted by streptozotocin," Diabetologia. 52(1):115-124 (2009).
Zhang et al., "Silencing miR-106b improves palmitic acid-induced mitochondrial dysfunction and insulin resistance in skeletal myocytes," Mol Med Rep. 11(5):3834-3841 (2015).
Zhang et al., "Expression of MiR-106b in the skeletal muscle of db/db mice and bioinformatics analysis," Yixue Yanjiusheng Xuebao Bianjibu. 26(3): 232-238 (2013) (2 pages) (Abstract Only).
Shi et al., "Differential expression of microRNAs in omental adipose tissue from gestational diabetes mellitus subjects reveals miR-222 as a regulator of ER(alpha) expression in estrogen-induced insulin resistance," Endocrinology. 155(5):1982-1990 (2014).
Coleman et al., "Elevation of miR-221 and -222 in the internal mammary arteries of diabetic subjects and normalization with metformin," available in PMC Jul. 15, 2014, published in final edited form as: Mol Cell Endocrinol. 374(0):125-129 (2013) (10 pages).

(Continued)

Primary Examiner — James D Schultz
(74) Attorney, Agent, or Firm — Clark & Elbing LLP

(57) ABSTRACT

The present invention is directed to provide nucleic acid molecules that promote proliferation of pancreatic islet β-cells. A proliferation promoting agent for promoting proliferation of pancreatic islet β-cells according to the present invention contains at least one of a nucleic acid molecule having SEQ ID NO: 1 or a nucleic acid molecule having SEQ ID NO: 2:

```
                                              (SEQ ID NO: 1)
UAAAGUGCUGACAGUGCAGAU (SEQ ID NO: 2)
AGCUACAUCUGGCUACUGGGUCUC.
```

13 Claims, 9 Drawing Sheets
Specification includes a Sequence Listing.

(56) References Cited

OTHER PUBLICATIONS

Ortega et al., "Profiling of circulating microRNAs reveals common microRNAs linked to type 2 diabetes that change with insulin sensitization," Diabetes Care. 37(5):1375-83 (2014).

Zgheib et al., "MicroRNA-29A is a key regulator of collagen homeostasis in human diabetic skin," Wound Rep Reg. 22: A70 (2014) (Abstract Only).

Chen et al., "Application of microRNAs in diabetes mellitus," J Endocrinol. 222(1):R1-R10 (2014).

Sato-Kunisada et al., "Enhanced expression of miR-199b-5p promotes proliferation of pancreatic Beta-cells by down-regulation of MLK3," MicroRNA. 5(1):57-65 (2016).

Zhou et al., "Regulation of insulin resistance by multiple miRNAs via targeting the GLUT4 signalling pathway," Cell Physiol Biochem. 38(5):2063-2078 (2016).

English Translation of the International Search Report for PCT Application No. PCT/JP2016/077575, dated Oct. 18, 2016 (2 pages).

English Translation of the Written Opinion for PCT Application No. PCT/JP2016/077575, dated Oct. 18, 2016 (7 pages).

\* cited by examiner (A) 24 hours later (B) 48 hours later (A)

(B)

(C) Liver (HE staining)

P: portal veins, C: central veins

Kidney (cortex) (HE staining)

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: DNA, RNA, or both DNA and RNA

<400> SEQUENCE: 1
uaaagugcug acagugcaga u                                            21

<210> SEQ ID NO 2
<211> LENGTH: 24
<212> TYPE: DNA
<213> ORGANISM: Artificial Sequence
<220> FEATURE:
<223> OTHER INFORMATION: DNA, RNA, or both DNA and RNA

<400> SEQUENCE: 2
agcuacaucu ggcuacuggg ucuc                                         24
```

NUCLEIC ACID MOLECULE

CROSS-REFERENCE TO RELATED DOCUMENTS

This application claims priority under Japanese Patent Application No. 2015-183339 filed on Sep. 16, 2015, and this first application is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 6, 2019 is named 51068-004001_Sequence_Listing_12.6.19_ST25 and is 711 bytes in size.

TECHNICAL FIELD

The present invention relates to nucleic acid molecules that promote the proliferation of pancreatic islet β-cells.

BACKGROUND ART

Pancreatic islet β-cells have been reported to be reduced or absent not only in patients with type 1 diabetes but also those with type 2 diabetes. Regeneration or promotion of the proliferation of pancreatic islet β-cells would thus be a promising therapeutic approach for these types of diabetes that can be contemplated.

The transplantation of bone marrow cells has recently been shown to promote the proliferation of pancreatic islet β-cells (see, Non-patent literatures 1 to 3). However, the mechanism underlying this remains unclear.

RELATED ART DOCUMENTS

Non-Patent Literatures

Non-patent literature 1: Hasegawa, Y. et al., Bone marrow (BM) transplantation promotes beta-cell regeneration after acute injury through BM cell mobilization, Endocrinology 148, 2006-2015, doi:en.2006-1351
Non-patent literature 2: Hess, D. et al., Bone marrow-derived stem cells initiate pancreatic regeneration, Nature biotechnology 21, 763-770, doi:10.1038/nbt841 (2003)
Non-patent literature 3: Nakayama, S. et al., Impact of whole body irradiation and vascular endothelial growth factor-A on increased beta cell mass after bone marrow transplantation in a mouse model of diabetes induced by streptozotocin, Diabetologia 52, 115-124, doi:10.1007/s00125-008-1172-z (2009)

SUMMARY OF THE INVENTION

Problems to be Solved by the Invention

An object of the present invention is to provide nucleic acid molecules that promote the proliferation of pancreatic islet β-cells.

Means to Solve the Problems

While the present inventors had been making extensive investigations in order to elucidate mechanisms underlying the phenomenon that the proliferation of pancreatic islet β-cells increases as a result of transplantation of bone marrow cells, the present inventors found that microRNAs miR-106b-5p and miR-222-3p regulate the promotion of pancreatic islet β-cell proliferation and the present invention was thus completed.

An aspect of the present invention is a proliferation promoting agent for promoting proliferation of pancreatic islet β-cells, containing at least one of a nucleic acid molecule having SEQ ID NO: 1, a nucleic acid molecule having SEQ ID NO: 2 and expression constructs of these nucleic acid molecules. The nucleic acid molecule may be an RNA molecule. It may be used to increase the proliferation of pancreatic islet β-cells after bone marrow transplantation. It may be administered intravenously.

Another aspect of the present invention is a therapeutic agent for diabetes containing any of the aforementioned proliferation promoting agents. It may be a therapeutic agent for type 1 diabetes and/or type 2 diabetes.

A further aspect of the present invention is a method of examining promotion of proliferation of pancreatic islet β-cells and includes the steps of synthesizing a nucleic acid molecule having a nucleotide sequence with 1 to 12 mutation(s) in SEQ ID NO: 1 or SEQ ID NO: 2 or an expression construct thereof; and determining whether or not the nucleic acid molecule or the expression construct thereof promotes proliferation of pancreatic islet β-cells.

A further aspect of the present invention is a method of obtaining a nucleic acid molecule or an expression construct thereof that promotes proliferation of pancreatic islet β-cells and includes the steps of synthesizing a plurality of nucleic acid molecules each having a nucleotide sequence with 1 to 12 mutation(s) in SEQ ID NO: 1 or SEQ ID NO: 2 or expression constructs thereof; determining whether or not each of the plurality of nucleic acid molecules or the expression constructs thereof promotes proliferation of pancreatic islet β-cells; and identifying a nucleic acid molecule or an expression construct thereof that promotes proliferation of pancreatic islet β-cells.

A further aspect of the present invention is a method of examining promotion of insulin secretion by pancreatic islet β-cells and includes the steps of synthesizing a nucleic acid molecule having a nucleotide sequence with 1 to 12 mutation(s) in SEQ ID NO: 1 or SEQ ID NO: 2 or an expression construct thereof; and determining whether or not the nucleic acid molecule or the expression construct thereof promotes insulin secretion by the pancreatic islet β-cells.

A further aspect of the present invention is a method of obtaining a nucleic acid molecule or an expression construct thereof that promotes insulin secretion by pancreatic islet β-cells and includes the steps of synthesizing a plurality of nucleic acid molecules each having a nucleotide sequence with 1 to 12 mutation(s) in SEQ ID NO: 1 or SEQ ID NO: 2 or expression constructs thereof; determining whether or not each of the nucleic acid molecules or the expression constructs thereof promotes insulin secretion by the pancreatic islet β-cells; and identifying a nucleic acid molecule or an expression construct thereof that promotes insulin secretion by the pancreatic islet β-cells.

In any one or more of the aforementioned methods, the nucleotide sequence of the nucleic acid molecule may be a sequence with 1 to 6 mutation(s) in SEQ ID NO: 1 or SEQ ID NO: 2, or a sequence with 1 to 3 mutation(s) in SEQ ID NO: 1 or SEQ ID NO: 2.

The sequences of SEQ ID NOs: 1 and 2 are as follows.

(SEQ ID NO: 1)
UAAAGUGCUGACAGUGCAGAU (SEQ ID NO: 2)
AGCUACAUCUGGCUACUGGGUCUC

EMBODIMENTS FOR CARRYING OUT THE INVENTION

Figure 1:
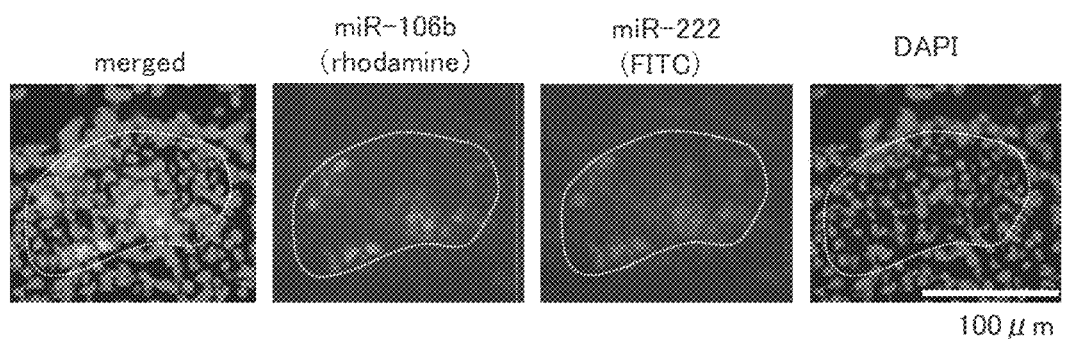
FIG. 1 shows photomicrographs indicating accumulation of microRNAs in the pancreatic islet of STZ-miRNAs mice in one example of the present invention.
Figure 1:
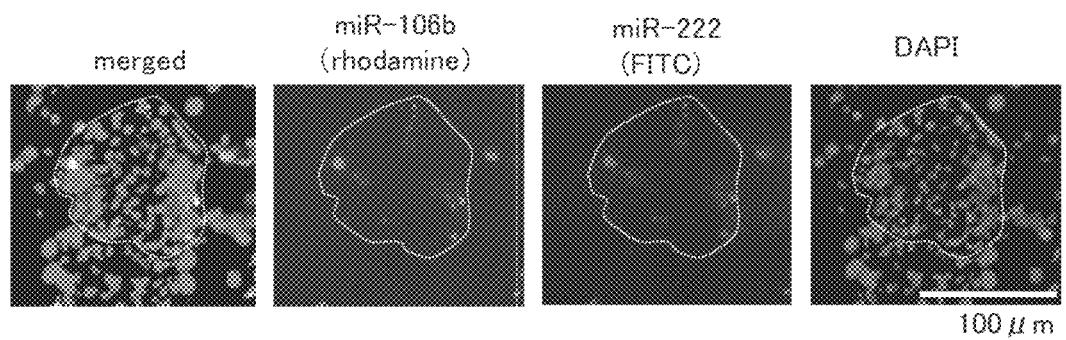

Embodiments of the present invention that was completed based on the aforementioned findings are described in detail along with examples.

Unless otherwise noted in embodiments and examples, all procedures used are according to standard protocols such as M. R. Green & J. Sambrook (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, if commercial reagent kits or measurement instruments are used, protocols attached thereto are used unless otherwise noted.

The objects, features, advantages, and ideas of the present invention are apparent to those skilled in the art from the description of this specification. Furthermore, those skilled in the art can easily reproduce the present invention from the description herein. The embodiments and specific examples described below represent preferable embodiments of the present invention, which are given for the purpose of illustration or explanation. The present invention is not limited thereto. It is obvious to those skilled in the art that various changes and modifications may be made according to the description of the present specification within the spirit and scope of the present invention disclosed herein.

==Nucleic Acid Molecules and Expression Constructs Thereof Used in the Present Invention==

Proliferation promoting agents for pancreatic islet β-cells, agents for enhancing insulin secretion, and therapeutic agents for diabetes, according to the present invention contain either or both of a nucleic acid molecule having the sequence of SEQ ID NO: 1 and a nucleic acid molecule having the sequence of SEQ ID NO: 2.

(SEQ ID NO: 1)
miR-106b-5p:   UAAAGUGCUGACAGUGCAGAU (SEQ ID NO: 2)
miR-222-3p:    AGCUACAUCUGGCUACUGGGUCUC.

The nucleic acid molecule may be composed of naturally-occurring nucleotides (i.e., ribonucleotides of RNA each having adenine, guanine, uracil, and cytosine as bases or deoxyribonucleotides of DNA each having adenine, guanine, thymine, and cytosine as bases) or a non-naturally-occurring nucleotides (e.g., nucleotides with inosine and α-enantiomers of a naturally-occurring nucleotide) or a chimeric molecule composed of both of them, but it is preferable that the nucleic acid molecule is RNA composed of ribonucleotides.

Nucleotides may be modified in a sugar and/or base (i.e., purine and/or pyrimidine) for the purpose of, for example, facilitating their uptake into cells or resisting against degradation by nucleases. As sugar modifications, for example, one or more hydroxyl groups may be substituted by halogen, alkyl, amine, or azide or may be etherified or esterified. Alternatively, the whole sugar may be replaced with sterically and electronically equivalent structures such as aza-sugars and carbocyclic sugar analogues. Modification of the base may, for example, be alkylation and/or acylation. Alternatively, the base may be subjected to heterocyclic substitution.

Proliferation promoting agents for pancreatic islet β-cells, agents for enhancing insulin secretion, and therapeutic agents for diabetes, according to the present invention may contain an expression construct capable of expressing either or both of the nucleic acid molecule having the sequence of SEQ ID NO: 1 and the nucleic acid molecule having the sequence of SEQ ID NO: 2. This expression construct includes an expression vector and an insertion which, when expressed, constitutes the nucleic acid molecule. As the expression vector, a known vector can be used. It may be a plasmid vector or a viral vector. Examples of the viral vector include an adenovirus vector, an adeno-associated viral vector, and a retrovirus vector. A promoter in the expression vector is not limited but may be a constitutive promoter such as a CMV promoter, an RSV promoter, an SV40 promoter, and an actin promoter or a conditional promoter such as an HSP promoter. It is, however, preferable that the promoter is the one that specifically functions in pancreatic islet β-cells, such as an insulin promoter.

==Proliferation Promoting Agents for Pancreatic Islet β-Cells==

Proliferation promoting agents for pancreatic islet β-cells according to the present invention contain either or both of the nucleic acid molecule having the sequence of SEQ ID NO: 1 and the nucleic acid molecule having the sequence of SEQ ID NO: 2 or the expression construct thereof. The proliferation promoting agents may be used for any applications such as experimental reagents and pharmaceutical agents.

For an experimental reagent, cells can be grown by introducing the nucleic acid molecule or the expression construct thereof described above into pancreatic islet β-cells cultured in vitro. The introduction method is not specifically limited and known transfection, lipofection, or electroporation can be used.

For a pharmaceutical agent, they can be used in vivo, in particular as agents for enhancing insulin secretion, therapeutic agents for diabetes, and therapeutic agents for diabetes complications. The target to which the nucleic acid molecule or the expression construct thereof is administered may be a human or any animal including a mouse which is suffering from the aforementioned diseases. Hereinafter, methods of using them is described in detail for an exemplified therapeutic agent for diabetes.

==Therapeutic Agents for Diabetes==

A therapeutic agent for diabetes according to the present invention contains either or both of the nucleic acid molecule having the sequence of SEQ ID NO: 1 and the nucleic acid molecule having the sequence of SEQ ID NO: 2.

The therapeutic agent for diabetes may be in any dosage form such as, for oral administration, a tablet, capsule, powder, granule, pill, liquid, emulsion, suspension, solution, alcoholic agent, syrup, extract, and elixir. Examples of parenteral preparations include injections such as subcutaneous injections, intravenous injections, intramuscular injections, and intraperitoneal injections; transdermal applicators or patches, ointments or lotions; sublingual preparations for buccal administration and oral patches; and aerosols for nasal administration; and suppositories, but are not limited thereto. These pharmaceutical formulations can be produced by known methods commonly used to produce pharmaceutical formulations. Agents according to the present invention may be in a sustained or sustained release dosage form.

In preparing solid pharmaceutical formulations for oral use, tablets, coated tablets, granules, powders or capsules can be produced using a routine method after adding an excipient and, if necessary, a binder, a disintegrating agent, a lubricant, a coloring agent, a corrigent, an odor masking agent and others to the active ingredient(s). Such additives may be those commonly used in the art. Examples of the excipient include lactose, white sugar, sodium chloride, glucose, starch, calcium carbonate, kaolin, microcrystalline cellulose, and silicic acid. Examples of the binder include water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, and polyvinyl pyrrolidone. Examples of the disintegrating agent include dry starch, sodium alginate, agar powder, sodium bicarbonate, calcium carbonate, sodium lauryl sulfate, stearic acid monoglyceride, and lactose. Examples of the lubricant include purified talc, stearates, borax, and polyethylene glycol. Examples of the corrigent include sucrose, orange peel, citric acid, and tartaric acid.

When liquid pharmaceutical formulations for oral use are prepared, a corrigent, a buffer, a stabilizer, an odor masking agent or others is added to the active ingredient and thus oral liquid preparations, syrups, or elixirs can be produced using a routine method. One or more of the aforementioned corrigents may be used in this case. Examples of the buffer include sodium citrate and examples of the stabilizer include tragacanth, gum arabic, and gelatin.

When injections are prepared, a pH adjusting agent, a buffer, a stabilizer, an isotonic agent, a local anesthetic or others is added to the active ingredient and thus subcutaneous, intramuscular or intravenous injections can be produced using a routine method. Examples of the pH adjusting agent and the buffer include sodium citrate, sodium acetate, and sodium phosphate. Examples of the stabilizer include sodium pyrosulfite, ethylenediaminetetraacetic acid (EDTA), thioglycolic acid, and thiolactic acid. Examples of the local anesthetic include procaine hydrochloride and lidocaine hydrochloride. Examples of the isotonic agent include sodium chloride and glucose.

When suppositories are prepared, a carrier for pharmaceutical preparations known in the art such as polyethylene glycol, lanolin, cocoa butter, and fatty acid triglyceride, and if necessary, a surfactant such as Tween (registered trademark) are added to the active ingredient and thus they can be produced using a routine method.

When ointments are prepared, a base, a stabilizer, a wetting agent, a preservative and others that are commonly used are formulated, mixed with the active ingredient as necessary, and formed into ointments. Examples of the base include liquid paraffin, white petrolatum, white beeswax, octyldodecyl alcohol, and paraffin. Examples of the preservative include methyl paraoxybenzoate, ethyl paraoxybenzoate, and propyl paraoxybenzoate.

When patches are prepared, the aforementioned ointment, cream, gel, paste or the like may be applied to an ordinary support using a routine method. As the support, woven and non-woven fabrics made of cotton, spandex, or chemical fibers as well as films and foam sheets made of, for example, soft vinyl chloride, polyethylene or polyurethane are suitable.

The amount of the active ingredient contained in the pharmaceutical agent can appropriately be determined depending on, for example, the dosage of the active ingredient and the number of dosing. The dose is not specifically limited and may appropriately be selected depending on, for example, the effectiveness of the ingredients contained, the type of administration, the route of administration, the type of disease, the features of the subject (e.g., body weight, age, disease condition, whether or not other pharmaceutical agent (s) is/are used), and a judgement of a physician in charge. Typically, it is preferable that an appropriate dose is, for example, in the range of about 0.01 μg to 100 mg, preferably about 0.1 μg to 1 mg per kg of the subject's body weight. These doses can, however, be varied using conventional routine experiments for optimization well known in the art. The aforementioned dosage can be administered once to several times a day.

==Methods of Examining Promotion of the Proliferation of Pancreatic Islet β-Cells or Promotion of the Insulin Secretion by Pancreatic Islet β-Cells==

Methods of examining promotion of the proliferation of pancreatic islet β-cells or promotion of the insulin secretion by pancreatic islet β-cells according to the present invention includes the steps of producing a nucleic acid molecule having a nucleotide sequence with a mutation in SEQ ID NO: 1 or SEQ ID NO: 2 or an expression construct thereof; and determining whether or not the nucleic acid molecule or the expression construct thereof produced promotes the proliferation of pancreatic islet β-cells or the proliferation of insulin secretion by the pancreatic islet β-cells. Specific methods for this are described in detail below.

First, a nucleotide sequence with a mutation in SEQ ID NO: 1 or SEQ ID NO: 2 is designed. The sequence may have any number of nucleotide mutations, but the number is preferably 6 or less, more preferably 4 or less, more preferably 3 or less, yet more preferably 2 or less, and still more preferably one. A nucleic acid molecule having the nucleotide sequence designed in this way is synthesized. How the nucleic acid molecule is synthesized is not specifically limited, and it may be prepared using cells or chemically synthesized. When its expression construct is used, it is prepared by inserting a DNA having that nucleotide sequence into an expression vector or the like.

Whether or not the nucleic acid molecule or the expression construct thereof promotes the proliferation of pancreatic islet β-cells or insulin secretion may be determined using any one of appropriate methods. The nucleic acid molecule or the expression construct thereof may be introduced into cultured pancreatic islet β-cells to examine its ability of proliferation or insulin secretion of the pancreatic islet β-cells. Alternatively, it may be administered to an animal suffering from diabetes to examine, in vivo, its ability of increasing the proliferation of pancreatic islet β-cells or cause these cells to secrete insulin. The method of examining the ability of proliferation of cells is not specifically limited and examples include a method of counting the number of cells of Ki-67-positive cells. The method of examining the ability of insulin secretion is also not specifically limited and, for example, an insulin level in the supernatant of cultured cells or blood of an individual animal can be measured using an anti-insulin antibody.

A novel nucleic acid molecule or an expression construct thereof that promotes the proliferation or insulin secretion of pancreatic islet β-cells can be obtained by designing a plurality of nucleic acid molecules having different mutations or expression constructs thereof, examining the ability of the proliferation or insulin secretion of the pancreatic islet β-cells, identifying a nucleic acid molecule or an expression construct thereof having the ability, and selecting it.

EXAMPLES (1) Production of STZ Mice and microRNA-Administered Mice

Streptozotocin (STZ) (Sigma) was intraperitoneally administered to C57BL/6J mice (6-week old) at 50 mg/kg body weight for five consecutive days to induce hyperglycemia (hereinafter, referred to as STZ mice). Here, STZ solution prepared by dissolving it in 0.05 M citrate buffer (pH 4.5) was used.

On the other hand, equal volumes (0.025% by weight each) of a mixed solution of microRNAs having SEQ ID NOs: 1 and 2 labeled with rhodamine and FITC, respectively (which are referred to as miR-106b and miR-222, respectively) (Cosmo Bio Co., Ltd.) and AteloGene® Systemic Use (available from Koken, Product No. 1393) were mixed with each other.

First, STZ was administered on Day 1 to 5 to produce the STZ mice and a microRNA/atelocollagen mixed solution (200 µl) was injected into their tail veins on Day 5. Frozen sections of pancreas were prepared 24 hours later (on Day 6) or 48 hours later (on Day 7) and observed with a fluorescence microscope. As a result, as shown in FIG. 1, the injected microRNAs accumulated in pancreatic islets denoted by the dotted line in the figure at both (A) 24 hours and (B) 48 hours.

(2) Measurement of Fasting Glucose

STZ was first administered to the STZ mice on Day 1 and 200 µl of the microRNA/atelocollagen mixed solution (denoted as miRNAs in the figure) was injected into the tail veins of the STZ mice (hereinafter, referred to as STZ-miRNAs mice) on Day 5, 8, and 11. Fasting blood glucose was measured on Day 1, 5, 15, 20, 30, 40 and 50 after the first STZ administration. Specifically, the mice were not fed with food for 9 hours during the daytime. Blood was then collected from their tail veins at 0, 15, 30, 60 and 120 minutes, and blood glucose levels were measured using Glutest Mint (Sanwa Kagaku). As a comparative example, mirVana miRNA mimic Negative Control #1 [Ambion (denoted as NT in the figure)] which is a microRNA not affecting gene expression was used instead of the above microRNAs (hereinafter, referred to as STZ-NT mice). For control mice (healthy mice), 200 µl of 0.05 M citrate buffer (pH 4.5) without STZ and microRNA was injected to the control mice (healthy mice) instead of STZ, only for the first five days.

Figure 2:
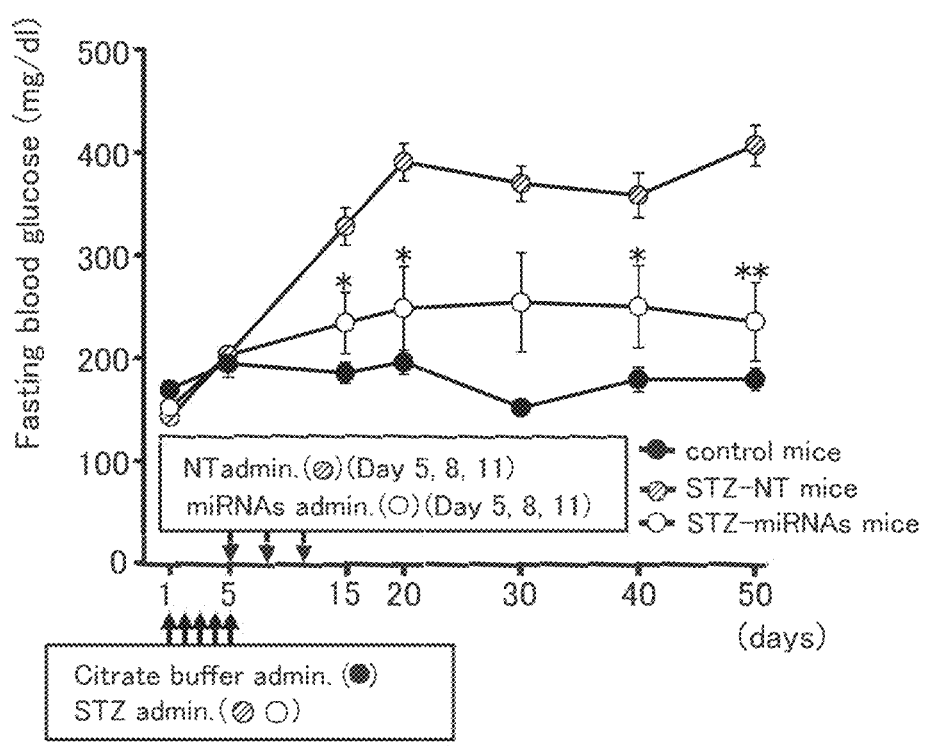
FIG. 2 is a diagram showing measurement results of STZ-miRNAs mice for fasting blood glucose in one example of the present invention.

As a result, as shown in FIG. 2, the fasting blood glucose level was significantly reduced on Day 15 after STZ administration in the STZ-miRNAs mice, compared with that in the STZ-NT mice and this reduced glucose level was maintained at least to Day 50 after STZ administration.

Thus, miR-106b and miR-222 have an effect of reducing fasting blood glucose of diabetic animals.

(3) Measurement of Blood Insulin Level and Pancreatic Insulin Content

Figure 3:
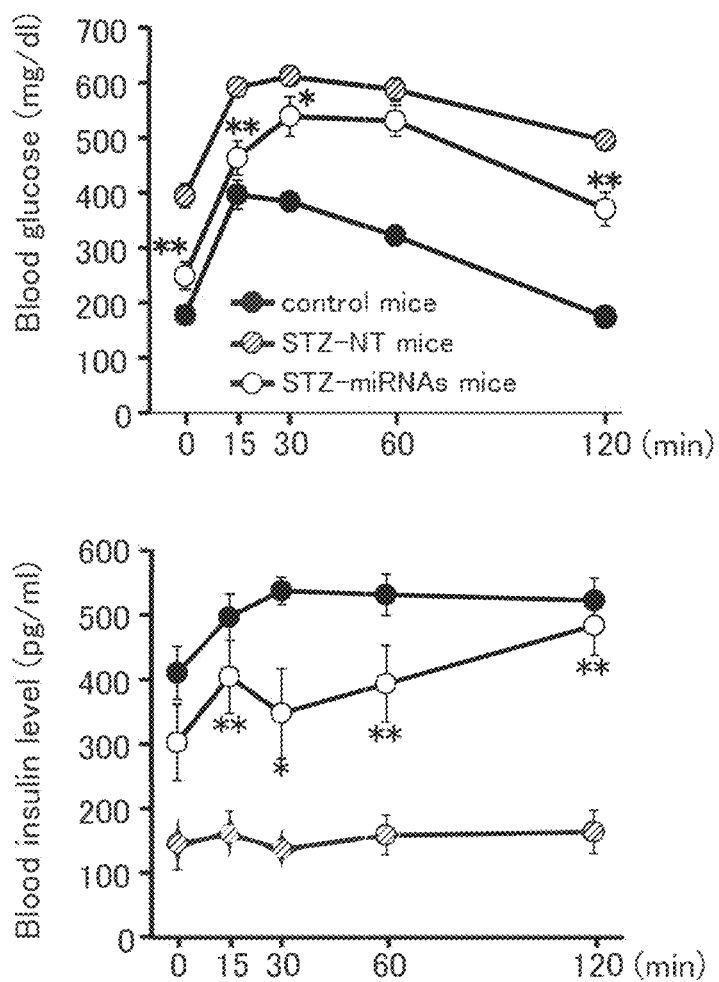
FIG. 3 is a diagram showing measurement results of STZ-miRNAs mice for blood insulin level in one example of the present invention.

A glucose tolerance test was performed on the mice produced in (2) on Day 45 after the STZ administration. As a result, glucose tolerances of STZ-miRNAs mice were improved as in (2). Serum insulin levels of these mice were measured using an ELISA kit (Morinaga Institute of Biological Science, Inc.), and the blood insulin levels were found to be increased in the STZ-miRNAs mice compared with those in the STZ-NT mice, as shown in FIG. 3.

Figure 4:
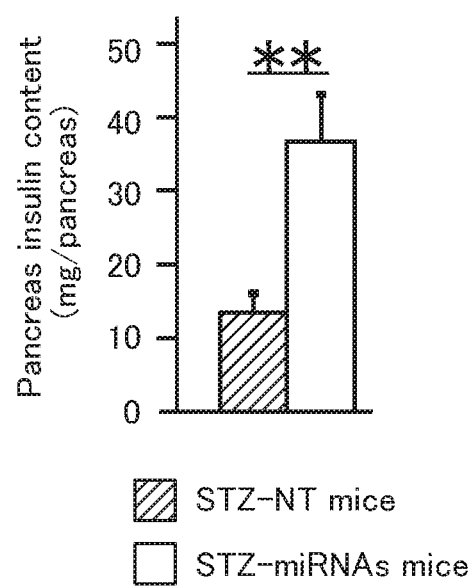
FIG. 4 is a diagram showing measurement results of STZ-miRNAs mice for pancreatic insulin content in one example of the present invention.

A portion of the pancreatic tissue was minced in HCl-ethanol (0.18 M HCl in 75% ethanol), left standing at −20° C. for 24 hours, and then subjected to sonication which was repeated twice. The supernatant was diluted with PBS containing 1 mM EDTA/1% BSA and the insulin contents in the pancreatic tissue were measured using an ELISA kit. The insulin contents in the tissue were also found to be increased in the STZ-miRNAs mice compared with those in the STZ-NT mice, as shown in FIG. 4.

Thus, miR-106b and miR-222 have an effect of improving glucose tolerance and increasing the blood insulin levels and pancreatic insulin contents of diabetic animals.

(4) Measurements of Number of Insulin-Positive Cells, Number of Glucagon-Positive α-Cells, and Number of Pancreatic Islet β-Cells Paraffin sections were prepared using the same portion of the spancreatic tissue used in (3), and insulin-expressing cells were detected using HRP-conjugated anti-insulin monoclonal antibody (Sigma) (2,000-fold dilution) and the DAB substrate. The number of insulin-positive cells increased in the STZ-miRNAs mice compared with that in the STZ-NT mice, as shown in FIG. 5A.

Figure 5:
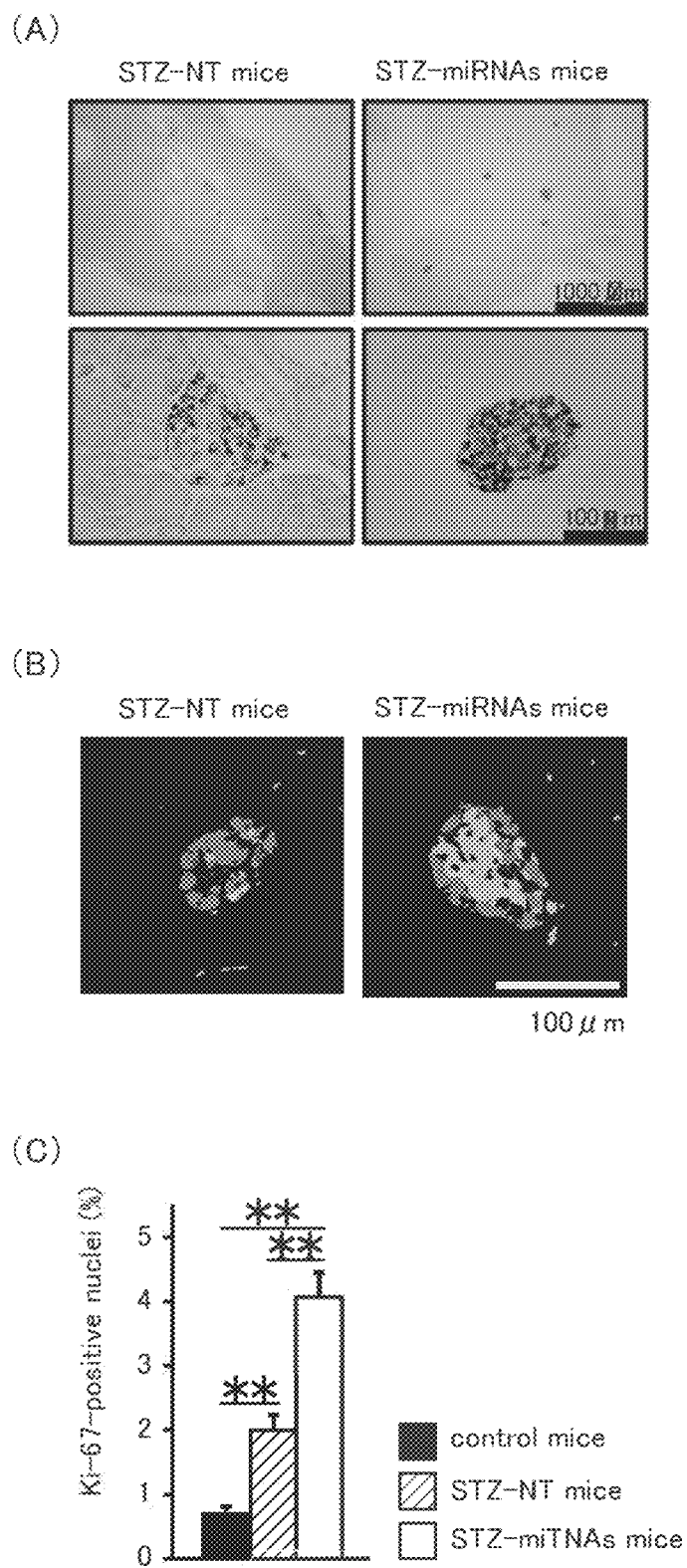
FIG. 5 is a diagram showing (A) the number of insulin-positive cells (dark areas), (B) the number of insulin-positive cells (light gray) and the number of glucagon-positive α-cells (dark gray), and (C) results of measurements of the number of pancreatic islet β-cells, in one example of the present invention.

On the other hand, by double staining using mouse anti-insulin monoclonal antibody (Sigma) (2,000-fold dilution) and a rabbit anti-glucagon polyclonal antibody (Dako) (3,000-fold) as primary antibodies and Alexa Fluor 488-labeled goat anti-mouse IgG and Alexa Fluor 546-labeled goat anti-rabbit IgG as secondary antibodies, the number of insulin-positive β-cells was found to be increased while the number of glucagon-positive α-cells was found to be decreased in the STZ-miRNAs mice compared with those in the STZ-NT mice, as shown in FIG. 5B.

Similarly, to detect proliferating cells of pancreatic islet β-cells, Ki-67-positive cells were detected using rabbit anti-Ki-67 (D3B5) monoclonal antibody (CST) (1,000-fold dilution) and the number of these cells was measured. The percentage of Ki-67-positive cells was found to be significantly increased in the STZ-miRNAs mice compared with that in the STZ-NT mice, as shown in FIG. 5B. Apoptosis was examined using the TUNEL assay but no differences were observed among the three, the STZ-miRNAs mice, the STZ-NT mice, and the control mice.

Thus, miR-106b and miR-222 have an effect of promoting the proliferation of pancreatic islet β-cells and increasing the insulin-positive cells in the pancreas.

(5) Measurements of Body Weight and Fat Accumulation

Figure 6:
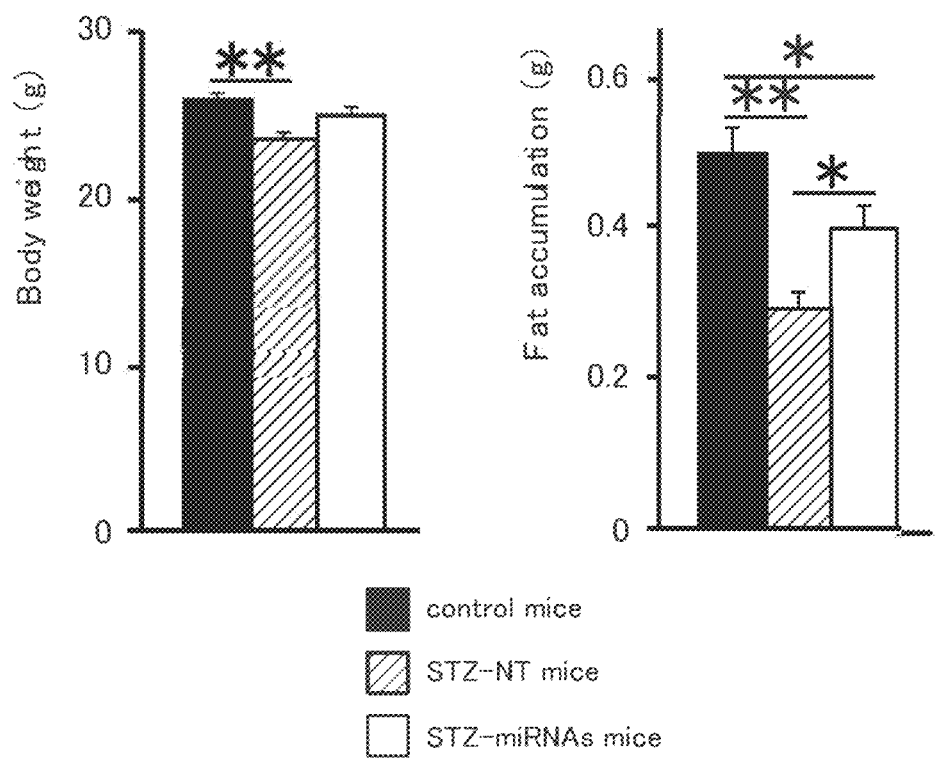
FIG. 6 is a diagram showing measurement results of STZ-miRNAs mice for the body weight and fat accumulation in one example of the present invention.

The body weights of the STZ-miRNAs mice and the STZ-NT mice were measured on Day 50 after the STZ administration. Their epididymal white adipose tissue was then removed and weighed. As a result, as shown in FIG. 6, the body weight and fat accumulation were reduced in the STZ-NT mice whereas the loss of body weight and fat accumulation were improved in the STZ-miRNAs mice. This effect is considered to result from the improvement in the diabetic conditions through treatment using miR-106b and miR-222.

(6) Administration of miR-222 Alone

Instead of the mixed solution of miR-106b and miR-222 (each 0.025% by weight) described in (1), a solution of 0.050% by weight of mir222 (Cosmo Bio Co., Ltd.) was injected into mice (hereinafter, denoted as STZ-mir222RNA mice) and fasting blood glucose was measured as in (2).

Figure 7:
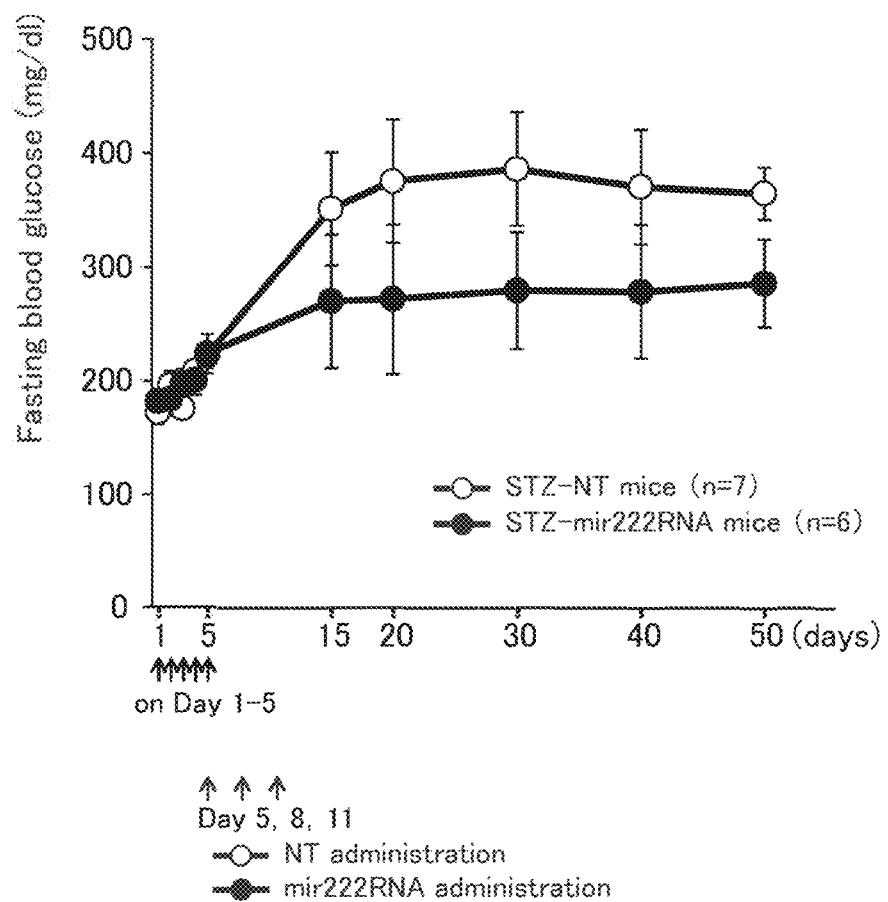
FIG. 7 is a diagram showing measurement results of STZ-mir222 RNA mice for fasting blood glucose level in one example of the present invention.

As a result, as shown in FIG. 7, in the STZ-mir222RNA mice, the fasting blood glucose was significantly reduced on Day 15 after STZ administration compared with that in the STZ-NT mice and this reduced glucose level was maintained at least to Day 50 after STZ administration.

(7) Effect of miR-106b/222 on the Proliferation of Pancreatic Islet β-Cells In Vitro In this example, the effect of miR-106b/222 on the proliferation of pancreatic islet β-cells in vitro was examined.

Forty islets isolated from the pancreas of mice using a collagenase perfusion method were dispersed by trypsin treatment and seeded on plates in vitro. A total of 20 pmol of miR-106b/miR-222 (10 pmol each) was transfected into the cells using Lipofectamine™ RNAiMAX Transfection Reagent. After 72 hours of culture, the cells were harvested and the expression, on the mRNA level, of Ki-67, which is a marker of cell proliferation, was measured using the real-time PCR.

Figure 8:
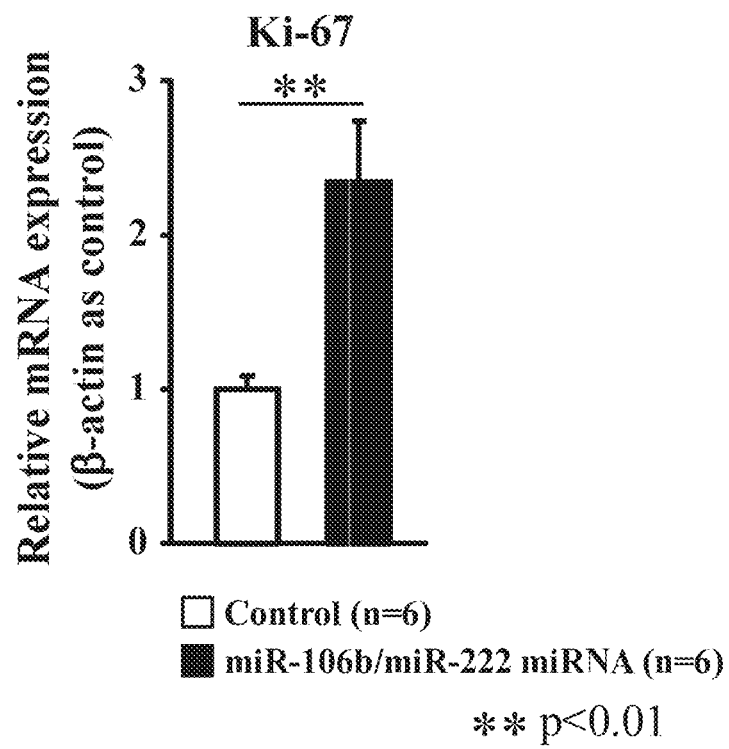
FIG. 8 is a diagram showing results of examining the effect of miR-106b/222 on the proliferation of pancreatic islet β-cells in vitro in one example of the present invention.

As shown in FIG. 8, in the cells transfected with the miR-106b/222 mixture, the Ki-67 expression level significantly increased.

Thus, miR-106b/222 also promotes the proliferation of pancreatic islet β-cells among the pancreatic cells in vitro.

(8) Effect of miR-106b/miR-222 on Liver and Kidneys

In this example, the influence of miR-106b/miR-222 on the liver and kidneys was examined.

Figure 9:
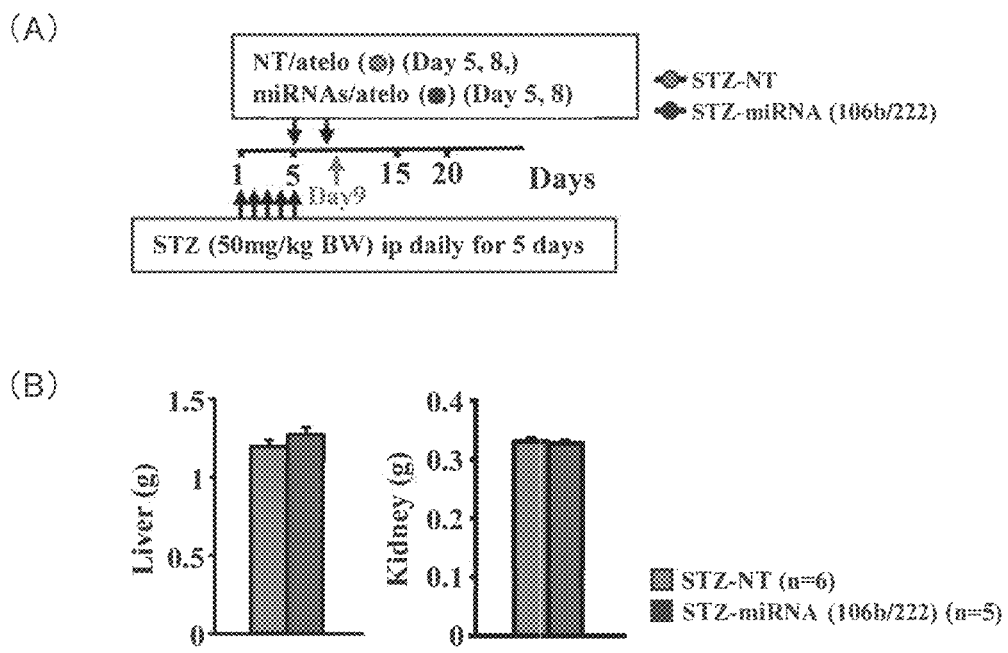
FIG. 9 is a diagram showing results of examining the effect of miR-106b/miR-222 on the liver and kidneys in one example of the present invention.
Figure 9:
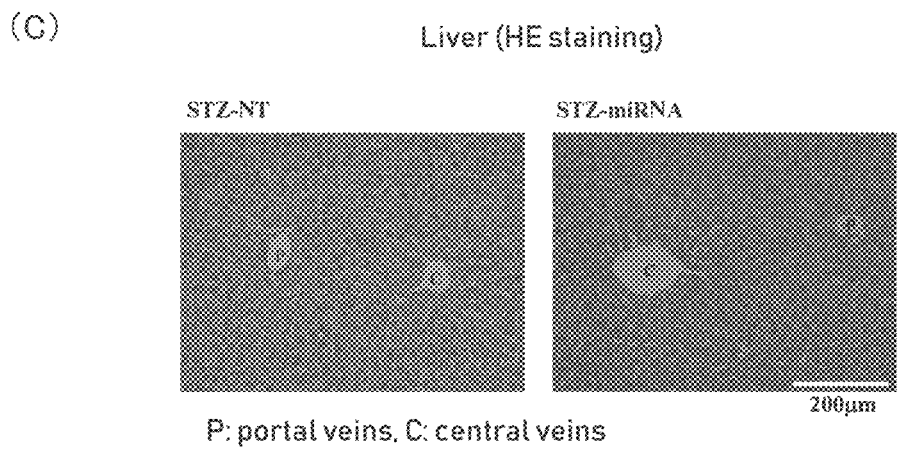
Figure 9:
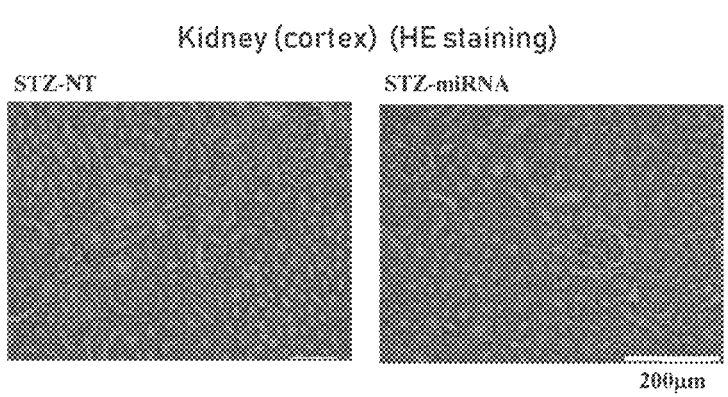

First, as shown in FIG. 9A, 200 μl of miR-106b/miR-222 microRNA/atelocollagen mixed solution (miRNAs/atelo) (5 mice) or negative control miRNA/atelocollagen mixed solution (NT/atelo) (6 mice) as a control (the mice are referred to as STZ-miRNA (106b/222) and STZ-NT, respectively) were injected into STZ mice, to which STZ (50 mg/kg body weight) had been administered by intraperitoneal injection on Day 1 to 5, via the tail vein on Day 5 and 9. On Day 9, their livers and kidneys were weighed. In addition, paraffin-embedded tissue sections were prepared and stained with HE, which were observed under a microscope. The results are shown in FIGS. 9B and 9C, respectively.

No significant differences were observed for the weights of the livers and kidneys between the STZ-miRNA (106b/222) and the STZ-NT (FIG. 9B). Furthermore, no differences were observed in histology between the STZ-miRNA (106b/222) and the STZ-NT (FIG. 9C).

It can thus be concluded that the administration of the miR-106b/miR-222 mixture does not adversely affect the liver and kidneys.

INDUSTRIAL APPLICABILITY

The present invention made it possible to provide nucleic acid molecules that promote the proliferation of pancreatic islet β-cells.

The invention claimed is:

1. A method for promoting proliferation of pancreatic islet β-cells, comprising:
   administering, to the pancreatic islet β-cells, an effective amount of either or both of a nucleic acid molecule having SEQ ID NO: 1 and a nucleic acid molecule having SEQ ID NO: 2:

UAAAGUGCUGACAGUGCAGAU (SEQ ID NO: 1)

AGCUACAUCUGGCUACUGGGUCUC. (SEQ ID NO: 2)

2. The method according to claim 1, wherein a part or all of nucleotides of the nucleic acid molecule is replaced with deoxyribonucleotides or non-naturally-occurring nucleotides.

3. The method according to claim 1, wherein:
   an expression construct of the nucleic acid molecule is administered to the pancreatic islet β-cells.

4. The method according to claim 1, wherein the method is used for promoting proliferation of pancreatic islet β-cells after bone marrow transplantation.

5. The method according to claim 1, wherein the nucleic acid molecule is administered intravenously.

6. A therapeutic method for a patient with diabetes comprising administering, to the patient, an effective amount of either or both of a nucleic acid molecule having SEQ ID NO: 1 and a nucleic acid molecule having SEQ ID NO: 2:

UAAAGUGCUGACAGUGCAGAU (SEQ ID NO: 1)

AGCUACAUCUGGCUACUGGGUCUC. (SEQ ID NO: 2)

7. The therapeutic method according to claim 6, wherein the diabetes is type 1 diabetes and/or type 2 diabetes.

8. The method of claim 1, wherein an effective amount of the nucleic acid molecule having SEQ ID NO: 1 is administered.

9. The method of claim 1, wherein, an effective amount of the nucleic acid molecule having SEQ ID NO: 2 is administered.

10. The method of claim 1, wherein an effective amount of the nucleic acid molecule having SEQ ID NO: 1 and an effective amount of the nucleic acid molecule having SEQ ID NO: 2 are administered.

11. The therapeutic method of claim 6, wherein an effective amount of the nucleic acid molecule having SEQ ID NO: 1 is administered.

12. The therapeutic method of claim 6, wherein, an effective amount of the nucleic acid molecule having SEQ ID NO: 2 is administered.

13. The therapeutic method of claim 6, wherein an effective amount of the nucleic acid molecule having SEQ ID NO: 1 and an effective amount of the nucleic acid molecule having SEQ ID NO: 2 are administered.

* * * * *